US009340809B2

(12) United States Patent
Hilditch et al.

(10) Patent No.: US 9,340,809 B2
(45) Date of Patent: May 17, 2016

(54) MICROBIAL CONVERSION OF SUGAR ACIDS AND MEANS THEREIN

(71) Applicant: VALTION TEKNILLINEN TUTKIMUSKESUS, Espoo (FI)

(72) Inventors: Satu Hilditch, Helsinki (FI); Merja Penttilä, Helsinki (FI); Peter Richard, Helsinki (FI)

(73) Assignee: Teknologian Tutkimuskeskus VTT Oy, Espoo (FI)

( * ) Notice: Subject to any disclaimer, the term of this patent is extended or adjusted under 35 U.S.C. 154(b) by 68 days.

(21) Appl. No.: 14/062,121

(22) Filed: Oct. 24, 2013

(65) Prior Publication Data

US 2014/0308715 A1 Oct. 16, 2014

Related U.S. Application Data

(60) Division of application No. 11/947,023, filed on Nov. 29, 2007, now abandoned, which is a continuation of application No. PCT/FI2006/050217, filed on May 29, 2006.

(30) Foreign Application Priority Data

May 30, 2005 (FI) ..................................... 20055263

(51) Int. Cl.
| | |
|---|---|
| *C12P 7/44* | (2006.01) |
| *C12P 21/06* | (2006.01) |
| *C12N 1/20* | (2006.01) |
| *C12N 1/00* | (2006.01) |
| *C12N 9/00* | (2006.01) |
| *C07H 21/04* | (2006.01) |
| *C12P 19/02* | (2006.01) |
| *C12N 9/88* | (2006.01) |
| *C12P 7/58* | (2006.01) |

(52) U.S. Cl.
CPC . *C12P 19/02* (2013.01); *C12N 9/88* (2013.01); *C12P 7/58* (2013.01); *Y02P 20/52* (2015.11)

(58) Field of Classification Search
None
See application file for complete search history.

(56) References Cited

FOREIGN PATENT DOCUMENTS

| WO | 97/29194 | 8/1997 |
|---|---|---|
| WO | 03/060136 | 7/2003 |

OTHER PUBLICATIONS

Whisstock et al. Quaterly Reviews of Biophysics, 2003, "Prediction of protein function from protein sequence and structure", 36(3): 307-340.
Chico et al. Semi-rational approaches to engineering enzyme activity: combining the benefits of directed evolution and rational design, Curr Opin Biotechnol. Aug. 2005; 16(4):378-84. Review.
Witkowski et al. Conversion of a beta-ketoacyl synthase to a malonyl decarboxylase by replacement of the active-site cysteine with glutamine, Biochemistry. Sep. 7, 1999;38(36):11643-50.
Agius et al., "Engineering increased vitamin C levels in plants by overexpression of a D-galacturonic acid reductase," *Nature Biotech.*, 21:177-181 (2003).
Buchanan et al., "An extremely thermostable aldolase from Sulfolobus solfataricus with specificity for nonphosphorylated substrates," *Biochem. J.*, 343:563-570 (1999).
Galagan et al., Hypothetical protein NCU07064.1 retrieved from EBI, source: *Neurospora crassa*, Database accession No. Q7S6F9 (2003), Da Tasase UniProtKB/TrEMB.
Kilgore et al., "Catabolism of galacturonic and glucuronic acids by *Erwinia cartovora*," *J. Biol. Chem.*, 234:2227-2235 (1959).
Kuorelahti et al., "Identification in the Mold *Hypocrea jecorina* of the First Fungal D-Galacturonic Acid Reductase," *Biochem.*, 44:11234-11240 (2005).
Martens-Uzunova et al., *Fungal Genetics Newsletter*, 52(Suppl.):93, § 185, XXII Fungal Genetics Conference, Mar. 15-20, 2005, Pacific Grove, CA.
Niu et al., "Microbial Synthesis ofthe Energetic Material Precursor 1,2,4-Butanetriol," *J. Am. Chem. Soc.*, 125:12998-12999 (2003).
Palleroni and Doudoroff, "Charaterization and Properties of 2-Keto-3-Deoxy-D-Arabonic Acid," *J. Biol. Chem.*, 223:499-508 (1956).
Palleroni et al., "Metabolism of carbohydrates by *Pseudomonas saccharophila*. III. Oxidation of D-arabinose," *J. Bacterol.*, 74:180-185 (1957).
Sealy-Lewis and Fairhurst, "An NADP$^+$-dependent glycerol dehydrogenase in *Aspergillus nidulans* is inducible by D-galacturonate," *Curr. Genet.*, 22:293-296 (1992).
Uitzetteret al., "Characterization of *Aspergillus nidulans* Mutants in Carbon Metabolism Isolated after D-galacturonate enrichment," *J. Gen. Microbiol.*, 132:1167-1172 (1986).
Visser et al., "Gycerol Uptake Mutants of the Hyphal Fungus *Aspergillus nidulans*," *J. Gen. Microbiol*, 134:655-659 (1988).
Witteveen et al., "Characterization of a glycerol kinase mutant of *Aspergillus niger*," *J. Gen. Microbiol.*, 136:1299-1305 (1990).
Receipt of original microorganism deposit and Viability Statement, Mascheroder Weg 1b, D-38124 Braunschweig, Germany, DSM 17214 (2 pages) (2005).
English abstract of WO 1997/029194.
Supplementary European Search Reporting relating to Application No. 06743559.4.
Kuorelahti, et al., L-galactonate Dehydratase is Part of the Fungal Path for D-galacturonic Acid Catabolism, D Molecular Microbiology (2006) 61(4), 1060-1068.
Elshafei, et al., Properties of Enzymes Involved in D-galactonatc Catabolism in Fungi, Antaine van Leeuwenhoek 67:211-216(1995).

*Primary Examiner* — Iqbal H Chowdhury
(74) *Attorney, Agent, or Firm* — Ladas & Parry LLP

(57) ABSTRACT

A DNA molecule comprising a fungal gene encoding an enzyme protein capable of converting L-galactonic acid into L-threo-3-deoxy-hexulosonic acid has been cloned and heterologously expressed. The enzyme is involved in the metabolic conversion of sugar acids, which are present in biological waste material such as sugar beet pulp and other pectin comprising material. A microorganism genetically modified to effectively express said enzyme may be used in fermenting biomaterial to desired end products such as ethanol. Alternatively, microorganisms in which the gene has been inactivated may be used to produce L-galactonic acid, which accumulates when the expression of the gene is prevented.

6 Claims, 3 Drawing Sheets

Figure 3a

```
1    ATGTCTGAAGTCACCATCACAGGCTTCAGGAGCCGCGATGTGCGGTTCCCCACGTCCCTA      1
1     M  S  E  V  T  I  T  G  F  R  S  R  D  V  R  F  P  T  S  L

61   GACAAGACGGGCTCGGATGCGATGAACGCTGCGGGCGACTATTCAGCGGCATACTGCATC     61
21    D  K  T  G  S  D  A  M  N  A  A  G  D  Y  S  A  A  Y  C  I

121  CTCGAGACTGATTCAGCGCACAGTGGTCATGGCATGgtcagcccccctttgaagcactct   121
41    L  E  T  D  S  A  H  S  G  H  G  M 157  gcgaagctgaagttccaagttgacagctttgctatagACATTCACCATTGGACGCGGAAA   181
53                                          T  F  T  I  G  R  G  N 180  CGACATCGTCTGCGCCGCCATCAACCACGTCGCGGACCGACTCAAGGGCAAGAAACTGTC   241
61    D  I  V  C  A  A  I  N  H  V  A  D  R  L  K  G  K  K  L  S 240  ATCACTAGTGGCCGACTGGGGCAAGACCTGGCGCTATCTGGTCAACGACAGCCAGCTGCG   301
81    S  L  V  A  D  W  G  K  T  W  R  Y  L  V  N  D  S  Q  L  R 300  GTGGATTGGCCCCGAAAAGGGCGTCATCCATCTTGCGCTCGGAGCCGTCGTCAACGCCGT   361
101   W  I  G  P  E  K  G  V  I  H  L  A  L  G  A  V  V  N  A  V 360  CTGGGACCTGTGGGCAAAGACGCTCAACAAGCCGGTTTGGCGCATCGTTGCCGACATGAC   421
121   W  D  L  W  A  K  T  L  N  K  P  V  W  R  I  V  A  D  M  T 420  GCCCGAGGAGTATGTCCGCTGCATCGACTTCCGCTACATTACCGACGCAATCACCCCCGA   481
141   P  E  E  Y  V  R  C  I  D  F  R  Y  I  T  D  A  I  T  P  E 480  GGAAGCCGTGGCGATGCTGCGCGAGCAGGAGGCCGGCAAGGCCAAGCGCATCGAGGAGGC   541
161   E  A  V  A  M  L  R  E  Q  E  A  G  K  A  K  R  I  E  E  A 540  TCTCCAGAACCGAGCGGTGCCTGCATACACAACAAGTGCCGGTTGGCTGGGATACGGAGA   601
181   L  Q  N  R  A  V  P  A  Y  T  T  S  A  G  W  L  G  Y  G  E 600  GGACAAGATGAAGCAGCTCCTGAGAGAGACGCTGGCTGCCGGATACAGACACTTCAAGGT   661
201   D  K  M  K  Q  L  L  R  E  T  L  A  A  G  Y  R  H  F  K  V 660  CAAGGTTGGCGGCAGCGTCGAGGAGGACCGAAGGCGCCTCGGCATTGCTCGCGAAATTCT   721
221   K  V  G  G  S  V  E  E  D  R  R  R  L  G  I  A  R  E  I  L 720  TGGTTTCGACAAGGGCAACGTTCTCATGGTCGATGCCAACCAGGTCTGGTCCGTTCCCGA   781
241   G  F  D  K  G  N  V  L  M  V  D  A  N  Q  V  W  S  V  P  E 780  AGCGATCGACTACATGAAGCAGCTCAGCGAGTACAAGCCCTGGTTCATTGAGGAGCCCAC   841
261   A  I  D  Y  M  K  Q  L  S  E  Y  K  P  W  F  I  E  E  P  T 840  CTCACCCGACGACATCATGGGCCACAAGGCCATTCGCGATGCCCTCAAGCCCTATGGCAT   901
281   S  P  D  D  I  M  G  H  K  A  I  R  D  A  L  K  P  Y  G  I 900  CGGCGTCGCTACCGGCGAGATGTGCCAGAACCGCGTCATGTTCAAGCAGCTGATCATGAC   961
301   G  V  A  T  G  E  M  C  Q  N  R  V  M  F  K  Q  L  I  M  T 960  GGGCGCCATCGACATCTGCCAGATTGATGCCTGCCGCCTCGGCGGCGTCAACGAAGTGCT  1021
321   G  A  I  D  I  C  Q  I  D  A  C  R  L  G  G  V  N  E  V  L 1020 GGCCGTCCTGCTCATGGCCAAGAAGTACGGTGTGCCCATTGTGCCGCATTCCGGCGGCGT  1081
341   A  V  L  L  M  A  K  K  Y  G  V  P  I  V  P  H  S  G  G  V 1080 GGGCCTTCCCGAGTACACCCAGCATCTGAGCACCATCGACTACGTGGTCGTCAGCGGCAA  1141
361   G  L  P  E  Y  T  Q  H  L  S  T  I  D  Y  V  V  V  S  G  K
```

```
1140    GCTTTCCGTCTTGGAGTTTGTAGACCACCTCCACGAGCACTTCTTGCATCCTTCAGTCAT    1201
381       L  S  V  L  E  F  V  D  H  L  H  E  H  F  L  H  P  S  V  I

1200    CAAGGACGGATACTACCAGACACCAACCGAGGCCGGCTACAGCGTTGAGATGAAGCCGGA    1261
401       K  D  G  Y  Y  Q  T  P  T  E  A  G  Y  S  V  E  M  K  P  E

1260    GAGCATGGACAAGTATGAGTATCCCGGCAAGAAGGGCGTAAGTTGGTGGACGACCGACGA    1321
421       S  M  D  K  Y  E  Y  P  G  K  K  G  V  S  W  W  T  T  D  E

1320    GGCTCTGCCCATCTTGAACGGAGAGAAGATCTGA                            1381
441       A  L  P  I  L  N  G  E  K  I  *
```

MICROBIAL CONVERSION OF SUGAR ACIDS AND MEANS THEREIN

RELATED APPLICATIONS

This application is a continuation of PCT application no. PCT/FI2006/050217, designating the United States and filed May 29, 2006; which claims the benefit of the filing date of Finnish application no. FI 20055263, filed May 30, 2005; each of which is hereby incorporated herein by reference in its entirety for all purposes.

FIELD

The present invention relates to enzymes involved in the conversion of sugar acids, and more precisely to an enzyme protein and its use and production. It further relates to DNA molecules encoding said enzymes, and to genetically engineered DNA-molecules and microorganisms comprising said DNA. The invention further relates to genetically modified microorganisms, wherein the enzyme-coding gene has been inactivated and to the use of such a microorganism.

BACKGROUND

Biological waste material from industry including agriculture contains sugars and their derivatives such as sugar acids. The conversion of such waste to useful products has been of interest and challenge in the field of biotechnology for a long time. D-galacturonic acid is the major component of pectin, a low price raw material enriched e.g. in sugar beet pulp, and a carbon source for microorganisms living on decaying plant material.

For bacteria a pathway is known consisting of 5 enzymes converting D-galacturonic acid (D-galacturonate) to pyruvate and D-glyceraldehyde 3-phosphate (FIG. 1). The intermediate metabolites are D-tagaturonate, D-altronate, D-erythro-3-deoxy-hexulosonic acid (2-keto-3-deoxy D-gluconate) and D-erythro-3-deoxy-hexulosonic acid 6-phosphate (2-keto-3-deoxy D-gluconate 6-phosphate). The enzymes are uronate isomerase (EC 5.3.1.12), an NADH utilizing D-tagaturonate reductase (EC 1.1.1.5), altronate dehydratase (EC 4.2.1.7), 2-keto-3-deoxy D-gluconatekinase (EC 2.7.1.45) and 2-keto-3-deoxy D-gluconate 6-phosphatealdolase (EC 4.1.2.14).

The pathway of FIG. 1 has only been described tier prokaryotic organisms, i.e. there are no reports about a similar pathway in eukaryotic microorganisms. A pathway must exist in eukaryotic microorganisms, since many species of yeast and mould can utilize and grow on D-galacturonate, however very little is known about such a pathway.

There are only a few studies on D-galacturonic acid catabolism in eukaryotic microorganisms. Uitzetter et al. 1986 (*J. Gen. Microbial.*, 132, 1167-1172) mutagenized the filamentous fungus *Aspergillus nidulans* and found that mutants lacking pyruvate dehydrogenase or pyruvate carboxylase activity were unable to grow on D-galacturonate, whereas a pyruvate kinase mutant was able to grow on D-galacturonate. This was interpreted to indicate that D-galacturonate is converted to pyruvate but not through phosphoenolpyruvate, i.e. this would be similar to the case in bacteria. Visser et al. (1988) *J. Gen. Microbial.*, 134:655-659), speculated that in *A. nidulans* D-galacturonic acid is catabolized through glyceraldehyde and pyruvate, which differs from the bacterial pathway in that the bacteria metabolize it through D-glyceraldehyde 3-phospate. It has further been suggested that D-galacturonic acid is metabolized through glycerol, since a glycerol kinase mutant had reduced growth on D-galacturonic acid (Witteveen, C. F. et al., (1990) *J. Gen. Microbial.*, 136:1299-1305), and an NADP dependent glycerol dehydrogenase was induced by D-galactronic acid (Sealy-Lewis, H. M. and Fairhurst, V., (1992) *Curr. Genet.*, 22:293-296).

There are no reports about genes, which are similar to the genes of the bacterial D-galacturonic acid pathway as shown in FIG. 1 in the genome of any eukaryotic microorganism of which the genome was sequenced. This suggests that there is a eukaryotic path for the catabolism of D-galacturonic acid, which is different from the bacterial path.

In fungi D-galacturonic acid has been suggested to be converted into galactonate by an aldoketo reductase, after which a dehydratase or racemase modifies galactonate to 2-keto-3-deoxygalactonate, and an aldolase splits 2-keto-3-deoxygalactonate into pyruvate and glyceraldehyde. Martens-Uzunova, E. et al., (*Fungal Genetics Newsletter*, vol. 52, Supplement (185), XXIII Fungal Genetics Conference Mar. 15-20, 2005, Pacific Grove, Calif.) have identified a cluster of co-expressed genes that encode the necessary putative aldoketo reductase, racemase and aldolase. No dehydratase was identified, nor do the authors explain the role of the racemase. In fact they do not mention whether said galactonate or said 2-keto-3-deoxygalactonate or said glyceraldehyde is in L- or D-configuration.

The present invention is based on finding a novel gene and enzyme involved in the fungal metabolism of D-galacturonic acid. This finding reveals a putative metabolic pathway of D-galacturonic acid. DNA comprising the gene may be used to produce genetically modified microorganisms, which are capable of effectively fermenting carbohydrates and their derivatives, such as sugar acids and their derivatives, from a biomaterial to obtain useful fermentation products, such as ethanol.

One aim of the invention is to provide an enzyme protein, which can be expressed by a host for the conversion of sugar acids and their derivatives to useful conversion products in a fermentation medium, or which is in the form of an enzymatic preparation for in vitro conversion of sugar acids and their derivatives to useful end products or intermediate products.

Another aim of the invention is to provide a genetically modified organism in which the expression of the gene is prevented, and which therefore is capable of accumulating the substrate of this enzyme.

The novel DNA molecule encodes a sugar acid dehydratase that is active on sugar acids, where the hydroxyl group of C2 is in L and the hydroxyl group of C3 is in D configuration in the Fischer projection. The enzyme does not exhibit activity with sugar acids, where the hydroxyl group of C2 is in D and the hydroxyl group of C3 is in L configuration. Such dehydratases are previously known e.g. from Niu et al. (*J. Am. Chem. Soc.*, (2003) 125:12998-12999), who described a dehydratase which is active on L-arabonic acid and D-xylonic acid. Another example is the D-gluconate dehydratase that is active in the non-phosphorylated Entner-Doudoroff pathway (see e.g. Buchanan et al. (1999) *Biochem. J.*, 343:563-570).

In a crude extract of the bacterium *Pseudomonas saccharophila* enzyme activity converting D-arabonic acid has been found, and the reaction product was believed to be 2-keto-3-deoxy-D-arabonic acid (Palleroni, N. J. and Doudoroff, M., (1956) *J. Biol. Chem.*, 223:499-508). However, no gene was isolated nor expressed.

SUMMARY

The invention provides an isolated DNA molecule comprising a gene encoding an enzyme protein capable of converting L-galactonic acid into L-threo-3-deoxy-hexulosonic acid.

The invention further provides a genetically engineered DNA molecule comprising said DNA molecule, and a genetically modified microorganism transformed with said genetically engineered DNA molecule.

The invention still further provides an enzyme protein capable of converting L-galactonic acid into L-threo-3-deoxy-hexulosonic acid, and a method of producing said enzyme by cultivating the genetically modified microorganism under conditions allowing expression of said protein, and recovering the enzyme protein.

A method of converting L-galactonic acid or D-arabonic acid to L-threo-3-deoxy-hexulosonic acid, or D-glycero-3-deoxy-pentulosonic acid, respectively by contacting L-galactonic acid or D-arabonic acid with said enzyme protein is also provided.

The invention further encompasses the use of the novel enzyme protein for producing a desired compound from a material comprising a sugar acid or a derivative thereof, and an enzyme preparation comprising said enzyme.

The invention still further encompasses a genetically modified microorganism, wherein a gene encoding an enzyme protein capable of converting L-galactonic acid into L-threo-3-deoxy-hexulosonic acid has been inactivated, and a method of producing L-galactonic acid or D-arabonic acid using the genetically modified microorganism.

Other objects, details and advantages of the present invention will become apparent from the following drawings, detailed description and examples.

BRIEF DESCRIPTION OF THE DRAWINGS

FIGS. 3a and 3b shows the DNA sequence (SEQ ID NO:1) of the coding region and amino acid sequence (SEQ ID NO:2) for the L-galactonic acid dehydratase. The upper lane indicates the DNA sequence, capital letters are for the coding sequence and small letters for the intron sequence. The lower lane shows the amino acid sequence.

FIG. 4 shows the plasmid pBluekan7-1.NotI, which was used in deleting the L-galactonic acid dehydratase gene.

DETAILED DESCRIPTION OF CERTAIN PREFERRED EMBODIMENTS

Figure 1:
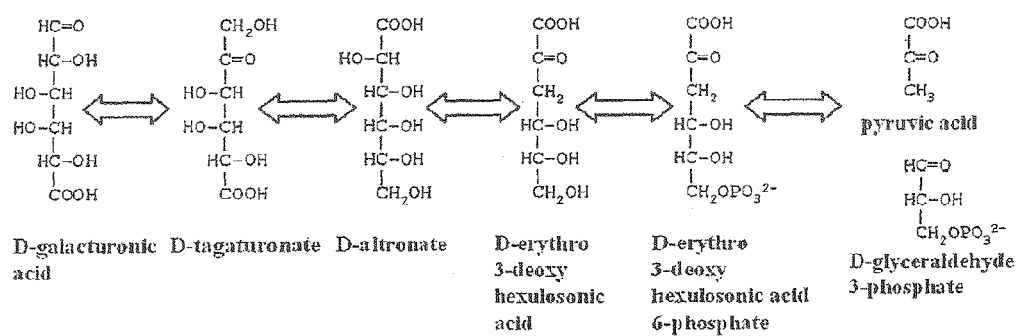
FIG. 1 shows the bacterial pathway for D-galacturonic acid utilization.
Figure 2:
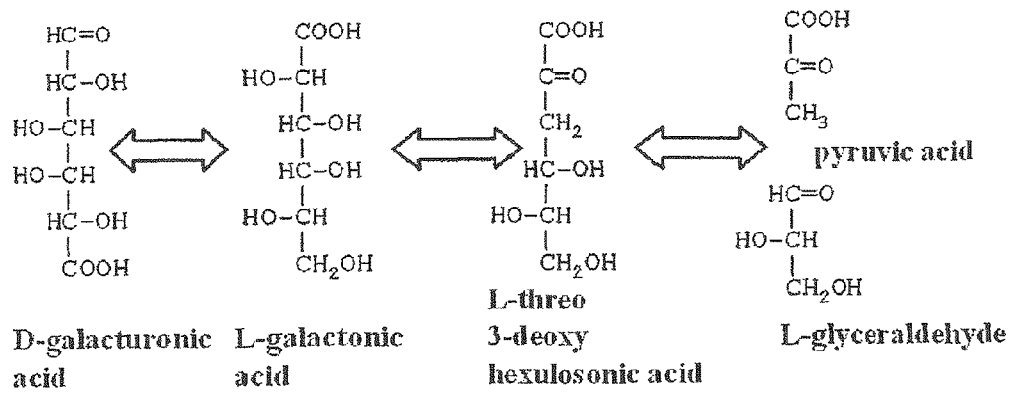
FIG. 2 shows the putative fungal pathway for D-galacturonic acid utilization.

A putative fungal pathway, which is distinctly different from the previously described bacterial pathway is summarized in FIG. 2. In this pathway D-galacturonic acid is first converted to L-galactonic acid by a D-galacturonic acid reductase. A gene for D-galacturonic acid reductase has been previously identified in plants and the enzyme activity has been described in yeast.

The second step where L-galactonic acid is converted to L-threo-3-deoxy-hexulosonic acid by a dehydratase is novel. We cloned the gene and expressed the activity in a heterologous host.

The third step is an aldolase reaction to make L-glyceraldehyde and pyruvate. L-glyceraldehyde might be converted to glycerol by an NADP glycerol dehydrogenase, since such an enzyme is induced on D-galacturonic acid.

The present invention provides for the first time an isolated DNA molecule, which comprises a gene encoding an enzyme protein, which exhibits L-galactonic acid dehydratase activity. The isolation and identification procedure are described below. The DNA sequence of the coding region and the amino acid sequence of the L-galactonic acid dehydratase is set forth in FIG. 3.

The novel DNA molecule encodes an L-galactonic acid dehydratase, which converts L-galactonic acid to L-threo-3-deoxy-hexulosonic acid (also called 2-keto-3-deoxy-L-galactonic acid). It is also active with D-arabonic acid (also called D-arabinoic acid), which is converted to D-glycero-3-deoxy-pentulosonic acid (also called 2-keto-3-deoxy-D-arabonic acid). More generally the enzyme is active on sugar acids or their derivatives, where the hydroxyl group of C2 is in L and the hydroxyl group of C3 is in D configuration in the Fischer projection. A sugar acid is a sugar oxidized at one or both ends. A "derivative of a sugar acid" can be any compound obtainable from a sugar acid or being a homologue of a sugar acid, and having a carboxyl group in C1, a hydroxyl group in L configuration in C2 and in D configuration in C3. The other C-atoms, and especially the end atom may comprise e.g. a methyl or an ester group. Preferably the sugar acid or its derivative comprises five to six C-atoms, especially six C-atoms.

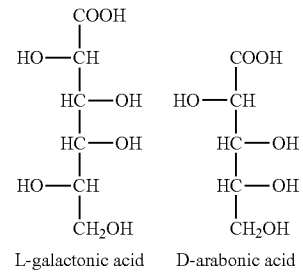 [SMILES: O=C(O)C(O)C(O)C(O)C(O)CO ; O=C(O)C(O)C(O)C(O)CO]

L-galactonic acid    D-arabonic acid

However, the enzyme does not exhibit activity with D-gluconic acid or D-xylonic acid, where the hydroxyl groups of C2 are in D and the hydroxyl groups of C3 are in L configuration in the Fischer projection.

It is evident that the terms "DNA molecule," "DNA sequence" and "nucleic acid sequence" include both genome DNA and cDNA (complementary DNA).

According to one embodiment of the invention, the isolated DNA sequence is derived from a *Hypocrea* (previously *Trichoderma*) species. According to one specific embodiment, the DNA is comprised in a deposit made at the International Depository Authority, Deutsche Sammlung von Mikroorganismen und Zellkulturen GmbH (DSMZ, Mascheroder Weg 1b, D-38124 Braunschweig) under the terms of the Budapest Treaty, on Mar. 30, 2005, under accession number DSM 17214. This deposit comprises the cDNA sequence having SEQ ID NO:1. The heterologous gene has been referred in the experimental part below as the Igd1 gene, and it is present on a multicopy plasmid under a constitutive yeast promoter, this strain the L-galactonic acid dehydratase is expressed. The deposited nucleic acid sequence originates from the mould strain *Hypocrea jecorina* (*Trichoderma reesei*) Rut C-30 (ATCC 56765). The deduced amino acid sequence of SEQ ID NO:1 is set forth as SEQ ID NO:2.

It is well known that genes from different organisms encoding enzymes with the same catalytic activity have sequence similarities and these similarities can be exploited in many ways by those skilled in the art to clone other genes from other organisms with the same or similar catalytic activity. Such genes are also suitable to practice the present invention. Therefore isolated DNA molecules obtainable from any organism, and especially from eukaryotic organisms such as fungi including yeast, plants, and animals including man are included in the invention. Preferably the DNA molecule is derived from a filamentous fungus.

DNA molecules of the invention may be obtained e.g. in silico by comparing nucleotide sequences. If such sequences are not available one can identify a conserved region in the nucleotide or amino acid sequence and clone a gene fragment using PCR techniques. After sequencing the fragment the complete gene can be obtained e.g. by using a cDNA library in a vector as described by Richard et al. (2001) *J. Biol. Chem.*, 276:40631-40637. Another way to identify an L-galactonic acid dehydratase gene is by conventional nucleic acid hybridization.

It is evident that many small variations in the nucleotide sequence of a gene do not significantly change the catalytic properties of the encoded protein. For example, many changes in the nucleotide sequence do not change the amino acid sequence of the encoded protein. Also an amino acid sequence may have variations, which do not change the functional properties of a protein, in particular they do not prevent an enzyme from carrying out its catalytic function. Such variations in the nucleotide sequence of DNA molecules or in an amino acid sequence are known as "functional equivalents," because they do not significantly change the function of the gene to encode a protein with a particular function, e.g. catalyzing a particular reaction or, respectively, change the particular function of the protein. Thus such functional equivalents, including fragments, of the nucleotide sequence of SEQ NO:1, and of the amino acid sequence of SEQ ID NO:2, respectively, are encompassed within the scope of the invention.

A functional equivalent of a nucleic acid sequence also includes nucleic acid sequences that are capable of hybridizing with the identified sequences under intermediate or high stringency conditions. For example, intermediate stringency hybridization can be performed in a hybridization mix containing 6×SSC (0.9 M in 0.09 M sodium citrate, pH 7), 0.5% sodium dodecyl sulfate (SDS), 5×Denhardts solution and 100 µg/ml of Herring Sperm DNA at 50° C. High stringency hybridization can be performed for example in the same hybridization mix at 68° C.

In a specific embodiment of the invention the enzyme protein comprises the amino acid sequence of SEQ ID NO:2 or a functional equivalent thereof. The functional equivalents include an amino acid sequence having at least 30%, preferably at least 50%, suitably at least 70%, e.g. at least 90% sequence identity to SEQ NO:2.

Furthermore, the invention is directed to a genetically engineered DNA molecule, i.e. a recombinant DNA, suitably to a vector, especially to an expression vector, which comprises the gene of the DNA molecule of the invention as described above so that it can be expressed in a host cell, i.e. a microorganism. In the recombinant DNA, the gene of the invention may be operably linked to a promoter. The vector can be e.g. a conventional vector, such as a virus, e.g. a bacteriophage, or a plasmid, preferably a plasmid. The construction of an expression vector is within the skills of an artisan. The general procedure and specific examples are described below.

The present invention also makes it possible to generate a genetically modified organism in which this L-galactonic acid dehydratase activity is absent. In such an organism L-galactonic acid is accumulating, i.e. such an organism would be suitable to produce L-galactonic acid from D-galacturonic acid or from other substrates from which L-galactonic acid can be derived. Correspondingly D-arabonic acid could be accumulated from D-arabinose. The knowledge of the DNA sequence for L-galacturonic acid dehydratase can be used to inactivate the corresponding gene or genes in a suitable microorganism. The gene can be inactivated e.g. by preventing its expression or by mutation or deletion of the gene or part thereof. There are various techniques for inactivating a gene. These techniques make use of the nucleotide sequence of the gene or of the nucleotide sequence in the proximity of the gene. The construction of a microorganism in which the gene for the L-galactonic acid dehydratase is prevented, mutated or deleted is within the skills of an artisan. Naturally the gene can be inactivated in any microorganism having said gene, and the invention makes it possible to identify such microorganisms. The general procedure and specific examples are described below.

L-galactonic acid may be used e.g. as an acidifier in food industry, or it may be used in cosmetics or in concrete industry.

The DNA molecule coding for an L-galactonic acid dehydratase can be transferred to any suitable microorganism or the gene coding for an L-galactonic acid dehydratase can be deleted in any suitable microorganism. A suitable microorganism can be suitable for the production of the desired conversion products or suitable to access the required substrates. An example is a fungal microorganism, which is efficiently utilizing D-galacturonic acid. In this microorganism the deletion of the L-galactonic acid dehydratase would lead to an accumulation of L-galactonic acid during the fermentation process. Another example is a microorganism where D-arabonic acid or L-galactonic acid is accumulating and the expression of the L-galactonic acid dehydratase facilitates the conversion of them to the desired reaction products.

Naturally, either the material to be utilized by said microorganisms of the invention comprises the sugar acid that is convertible in the presence of the L-galactonic acid dehydratase, or the microorganism is capable of expressing further genes to produce enzymes that are needed for the conversion of the starting material to a sugar acid utilizable by the said dehydratase expressed by the gene of the invention. The starting material is preferably of natural origin i.e. a biomaterial e.g. biomass comprising sugar, sugar acids or derivatives thereof. One example of suitable biomaterial is sugar beet pulp, which comprises pectin, which mainly consists of D-galacturonic acid. Also other pectin comprising materials may be used.

According to one embodiment of the invention biomass comprising a sugar acid or a derivative thereof is fermented by a microorganism transformed with a DNA molecule comprising a gene encoding an enzyme protein capable of converting L-galactonic acid into L-threo-3-deoxy-hexulosonic acid, and the desired compound produced is recovered. If the transformed microorganism further expresses an aldolase capable of converting L-threo-3-deoxy-hexulosonic acid into L-glyceraldehyde and pyruvate, and L-glyceraldehyde is further converted to e.g. glycerol, these metabolites can be converted the microorganism to ethanol, lactic acid or any other compound metabolically derivable from these metabolites using the metabolic pathway of that microorganism. Said pyruvate may also be further converted by the microorganism to ethanol through pyruvate decarboxylase and alcohol dehydrogenase, to lactic acid through lactate dehydrogenase, or to any other compound metabolically derivable from pyruvate.

The invention is not restricted to genetically modifying mould or yeast. The genes encoding L-galactonic acid dehydratase can be expressed in any organism such as bacteria, plants or higher eukaryotes by applying the genetic tools suitable and known in the art for that particular organism. The term "microorganism" should therefore be interpreted broadly to include also cell lines of higher organisms.

Conveniently the L-galactonic acid dehydratase is produced by recombinant technology. This denotes the isolation of a fragment comprising the dehydratase gene by amplification in a PCR reaction (Coen, D. M., (2001) "The polymerase chain reaction," published in: Ausubel, F. M., Brent, R., Kingston, R. E., More, D. D., Seidman, J. G., Smith, K. and Struhl, K. (eds.) *Current Protocols in Molecular Biology*, John Wiley & Sons. Inc., Hoboken, USA), or other recombinant DNA methods (Sambrook, J., Fritsch, E. F. and Maniatis, T. (1989) *Molecular Cloning: A Laboratory Manual*, 2nd edn. Cold Spring Harbor Laboratory, Cold Spring Harbor N.Y.), insertion of the gene under a strong promoter in an expression vector, transfer of the vector into suitable host cells and cultivation of the host cells in conditions provoking production of said enzyme. Methods for protein production by recombinant technology in different host systems are well known in the art (Gellissen, G. (ed.) (2005) *Production of Recombinant Proteins. Novel Microbial and Eukaryotic Expression System*, Wiley-VCH Verlag GmbH & Co. Weinheim, Germany). Alternatively only the strong promoter is operably linked to the dehydratase gene on the host's chromosome, whereby the expression of said gene is overexpressed. The expressed protein can be isolated and purified by conventional protein purification methods.

The invention is further directed to an enzyme preparation comprising the L-galactonic acid dehydratase. Such a preparation may be a crude cell extract of the genetically modified organism, or the enzyme may be further purified therefrom, whereby the preparation comprises at least the L-galactonic acid dehydratase in purified form. The preparation may also comprise other enzymes taking part in the catabolism of sugars or sugar acids or their derivatives.

Moreover, the invention provides the use of an L-galactonic acid dehydratase for the conversion of L-galactonic acid or D-arabonic acid or more generally for the conversion of sugar acids or their derivatives, where the hydroxyl groups of C2 and C3 are in L and D configuration, respectively, to the products described previously.

It is evident that in all cases when a sugar acid is described such as D-galacturonic acid, L-galactonic acid, L-threo-3-deoxy-hexulosonic acid, D-arabonic acid and all other acids, the description also includes the anionic form of the sugar acid i.e. D-galacturonate, L-galactonate, L-threo-3-deoxy-hexulosonate, D-arabonate or the corresponding anionic form of the acid, because in practice it is often difficult to distinguish between the dissociated and non dissociated form of the acid.

The invention is illustrated by the following non-limiting examples. It should be understood, however, that the embodiments given in the description above and in the example are for illustrative purposes only, and that various changes and modifications are possible within the scope of the invention.

EXAMPLE 1

Cloning of the L-Galactonic Acid Dehydratase

The *Hypocrea jecorina* (*Trichoderma reesei*) genome was screened for genes with homology to dehydratases. The open reading frames were then amplified by PCR and ligated to a yeast expression vector. For that purpose PCR primers containing BamHI restriction sites were designed to amplify the open reading frames. The PCR template was a *H. jecorina* cDNA library. The PCR product was ligated to a TOPO vector (Invitrogen). From the TOPO vector the BamHI fragment was released and ligated to a yeast expression vector. The expression vector was derived from the pYX212 plasmid (R&D Systems) by digesting it with EcoRI and XhoI to remove the ATG and HA-tag from the multiple cloning site and introducing a BamHI restriction site to the cloning site by inserting a EcoRI and SalI cut fragment from the pUC19 plasmid (Norrander, J., Kempe, T. and Messing, J. (1983) *Gene*, 26:101-106).

The resulting vector was then transformed to a strain of *Saccharomyces cerevisiae*. The resulting *S. cerevisiae* strain was then disintegrated by vortexing with glass beads and the yeast extract analyzed for L-galactonic acid dehydratase activity. To assay the L-galactonic acid dehydratase activity L-galactonic acid was mixed with the yeast extract and formation of reducing sugars followed using standard protocols. (Bernfeld, P. (1955) "Amylases, α and β," In: *Methods In Enzymology*, vol. 1, Colovick S. P., Kaplan, N. O. (eds.) Academic Press NY, pp 149-158).

Using the primers 5'-GGATCCACCATGTCTGAAGT-CACCAT-3' (SEQ ID NO:3) in sense direction and the primer 5'-GGATCCTCAGATCTTCTCTCCGTTCA-3' (SEQ ID NO:4) in antisense resulted in an active L-galactonic acid dehydratase after expression in *S. cerevisiae*. The gene was called Igd1.

The *S. cerevisiae* strain, which is overexpressing the L-galactonic acid dehydrogenase is called H3350 and is deposited with the deposition number DSM 17214.

EXAMPLE 2

Identification of the Reaction Product and Testing the Specificity of the L-Galactonic Acid Dehydratase L-galactonic acid was mixed with the yeast extract of strain H3350 as described in example 1. The reaction product was identified as a 2-keto-3-deoxy sugar acid in a chemical assay and quantified as described by Buchanan et al. (1999) *Biochem. J.*, 343:563-570. The protein concentration of the yeast extract in the reaction medium was 0.15 g/l and the initial L-galactonic acid concentration 10 mM. After 21 hours 1.04 mM of L-threo-3-deoxy-hexulosonic acid was formed.

To test the specificity of the enzyme the yeast extract as described before was mixed with the sugar acids D-gluconic acid, D-arabonic acid, D-xylonic acid, L-gulonic acid and L-galactonic acid. We followed the formation of reducing sugars as described in the example 1. Activity was observed with the sugar acids L-galactonic acid and D-arabonic acid.

EXAMPLE 3

Deletion of the L-Galactonic Acid Dehydratase in *H. jecorina*

Figures 3B, 4:
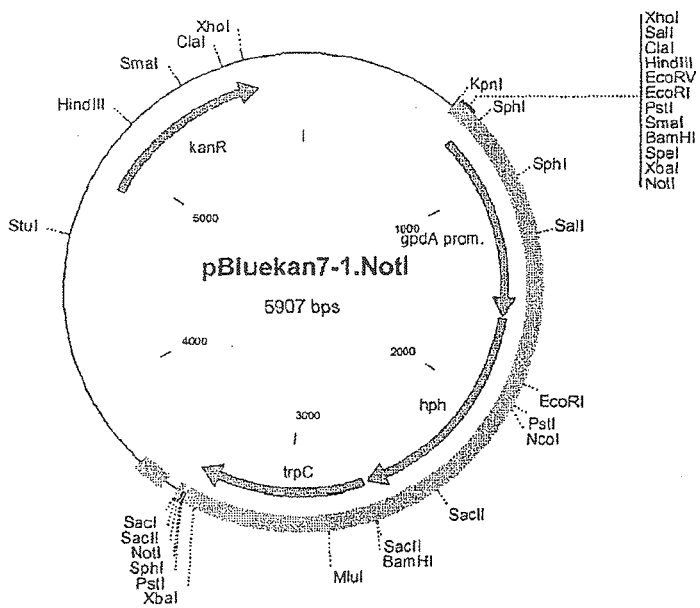

For the deletion of the Igd1 gene a deletion cassette was constructed. For the deletion cassette 1.5 kb areas from both sides of L-galactonic acid dehydratase gene were cloned and ligated to the pBluekan7-1.NotI plasmid (FIG. 4). The part upstream the Igd1 was cloned using the oligos 5'-GAGCT-CAAGCTTCCACGCAGTTGCTACTTCTA-3' (SEQ ID NO:5) and 5'-GAGCTCTGGTTATTTGGCAGAGCCGAC-3' (SEQ ID NO:6) introducing SacI and HindIII restriction sites. The SacI fragment was ligated to the SacI cloning site of the pBluekan7-1.NotI. The part downstream of the IgdI was cloned with the oligos 5'-ACTAGTGGGGCAAAGTTGGA-CATGAT-3° (SEQ ID NO:7) and 5'ACTAGTAAGCTTG-CAATACCTGGACCAAGCTA-3' (SEQ ID NO:8) introducing SpeI and HindIII restriction sites. The SpeI fragment was ligated to the SpeI site of the pBluekan7-1.NotI. The two DNA fragments were then ligated to the pBluekan7-1. NotI vector in such a way that the orientation of the two DNA fragments relative to each other was not changed and a gene for hygeromycin resistance was placed between the two fragments. The deletion cassette comprising the two DNA fragments and the hygeromycin resistance gene was then released by the HindIII digestion, transformed to *H jecorina* Rut C-30 strain and selected for hygeromycin resistance using standard protocols. The resulting strain was able to convert D-galacturonic acid to L-galactonic acid.

EXAMPLE 4

NMR Analysis of Reaction Product

L-galactonic acid was mixed with the yeast extract of strain H3350 as described in Example 1. The reaction product was identified by NMR.

The NMR experiments were carried out at 23° C. on a Varian Inova spectrometer operating on a proton frequency of 500 MHz. The spectral widths of the 1D $^1$H and $^{13}$C spectra were 5000 Hz and 30675 Hz, respectively. In DQFCOSY and TOCSY experiments, the spectral width was 3400 Hz and matrices of 1024×128 complex data points were acquired. The spinlock time in the TOCSY was 80 ms. In HSQC the spectral widths in $^1$H and $^{13}$C dimensions were 1654 Hz and 10000 Hz, respectively, and a matrix of 1024×256 complex data points was acquired. All 2D data matrices were zero-filled once in F1 and a cosine bell weighting function was applied in both dimensions prior to the Fourier transformation.

The structure of the reaction product was verified by NMR spectroscopy and the $^1$H and $^{13}$C chemical shifts of the product are given in Table 1. From 1D $^1$H spectrum of the reaction mixture the product signals were readily visible, and from 2D DQFCOSY and [$^1$H, $^{13}$C]HSQC experiments it was evident, that the product has a proton spin-system CH2-CH—CH—CH2, in which one of the CH2 has typical chemical shifts of a hydroxymethyl group and the second one has quite unique chemical shifts typical to CH2 groups close to a keto group or a hemi-acetal structure. The DEPT spectrum further confirmed that the molecule has two CH2 and two CH type carbon atoms. In addition to these four carbons, the $^{13}$C spectrum of the product revealed two additional carbon signals. One is on the carboxyl area close to the signal of the carboxyl carbon of the substrate and the other one (97.84 ppm) is typical for a quaternary carbon in hemi-acetal structure, like C2 signals sialic acids. The NMR results show that the reaction product is 2-keto-3-deoxy-galactonic acid and that it exists predominantly as a pyranose ring. Only signals of one anomer were detected, but it was not possible to determine, which one of two anomers it is.

TABLE 1

$^1$H and $^{13}$C NMR chemical shifts of the product 2-keto-3-deoxy-galactonic acid

| | δ (ppm)[a] | | δ (ppm)[b] |
|---|---|---|---|
| H3 | 1.789 | C1 | 177.53 |
| H3' | 2.162 | C2 | 97.84 |
| H4 | 3.859 | C3 | 40.22 |
| H5 | 3.604 | C4 | 70.13 |
| H6 | 3.606 | C5 | 71.92 |
| H6' | 3.801 | C6 | 64.18 |

[a]referenced to internal TSP (0 ppm)
[b]referenced to external acetone (31.5 ppm)

The invention claimed is:

1. A method of producing L-galactonic acid, said method comprising:

providing a fungal microorganism having a gene encoding L-galactonic acid dehydratase capable of converting L-galactonic acid into L-threo-3-deoxy-hexulosonic acid, inactivating said gene by preventing its expression or mutation or deletion of said gene or functional part thereof, and cultivating the obtained genetically modified micro-organism on a material comprising sugar, sugar acid or derivative thereof and recovering the accumulated L-galactonic acid using the obtained genetically modified microorganism for producing the L-galactonic acid.

2. The method of claim 1, wherein the microorganism is a microorganism which efficiently utilizes D-galacturonic acid.

3. The method of claim 1, wherein the genetically modified microorganism is cultivated on biomass.

4. The method of claim 1, wherein the genetically modified microorganism is cultivated on a substrate comprising D-galacturonic acid or another substrate from which L-galactonic acid can be derived, and the accumulated L-galactonic acid is recovered.

5. The method of claim 4, wherein the genetically modified microorganism is cultivated on a pectin comprising material.

6. The method of claim 1, wherein the gene is inactivated by deleting the whole gene or functional part thereof.

* * * * *

SEQUENCE LISTING

```
<160> NUMBER OF SEQ ID NOS: 8

<210> SEQ ID NO 1
<211> LENGTH: 1353
<212> TYPE: DNA
<213> ORGANISM: Hypocrea jecorina 1

<400> SEQUENCE: 1
atgtctgaag tcaccatcac aggcttcagg agccgcgatg tgcggttccc cacgtcccta      60
gacaagacgg gctcggatgc gatgaacgct gcgggcgact attcagcggc atactgcatc     120
ctcgagactg attcagcgca cagtggtcat ggcatgacat tcaccattgg acgcggaaac     180
gacatcgtct gcgccgccat caaccacgtc gcggaccgac tcaagggcaa gaaactgtca     240
tcactagtgg ccgactgggg caagacctgg cggtatctgg tcaacgacag ccagctgcgg     300
tggattggcc ccgaaaaggg cgtcatccat cttgcgctcg gagccgtcgt caacgccgtc     360
tgggacctgt gggcaaagac gctcaacaag ccggtttggc gcatcgttgc cgacatgacg     420
cccgaggagt atgtccgctg catcgacttc cgctacatta ccgacgcaat caccccgag      480 gaagccgtgg cgatgctgcg cgagcaggag gccggcaagg ccaagcgcat cgaggaggct     540
ctccagaacc gagcggtgcc tgcatacaca acaagtgccg gttggctggg atacggagag     600
gacaagatga agcagctcct gagagagacg ctggctgccg gatacagaca cttcaaggtc     660
aaggttggcg gcagcgtcga ggaggaccga aggcgcctcg gcattgctcg cgaaattctt     720
ggtttcgaca agggcaacgt tctcatggtc gatgccaacc aggtctggtc cgttcccgaa     780
gcgatcgact acatgaagca gctcagcgag tacaagccct ggttcattga ggagcccacc     840
```

-continued

```
tcacccgacg acatcatggg ccacaaggcc attcgcgatg ccctcaagcc ctatggcatc    900
ggcgtcgcta ccggcgagat gtgccagaac cgcgtcatgt tcaagcagct gatcatgacg    960
ggcgccatcg acatctgcca gattgatgcc tgccgcctcg gcggcgtcaa cgaagtgctg   1020
gccgtcctgc tcatggccaa gaagtacggt gtgcccattg tgccgcattc cggcggcgtg   1080
ggccttcccg agtacaccca gcatctgagc accatcgact acgtggtcgt cagcggcaag   1140
ctttccgtct tggagtttgt agaccacctc cacgagcact tcttgcatcc ttcagtcatc   1200
aaggacggat actaccagac accaaccgag gccggctaca gcgttgagat gaagccggag   1260
agcatggaca gtatgagta tcccggcaag aagggcgtaa gttggtggac gaccgacgag    1320
gctctgccca tcttgaacgg agagaagatc tga                               1353
```

<210> SEQ ID NO 2
<211> LENGTH: 450
<212> TYPE: PRT
<213> ORGANISM: Hypocrea jecorina

<400> SEQUENCE: 2

```
Met Ser Glu Val Thr Ile Thr Gly Phe Arg Ser Arg Asp Val Arg Phe
1               5                   10                  15

Pro Thr Ser Leu Asp Lys Thr Gly Ser Asp Ala Met Asn Ala Ala Gly
            20                  25                  30

Asp Tyr Ser Ala Ala Tyr Cys Ile Leu Glu Thr Asp Ser Ala His Ser
        35                  40                  45

Gly His Gly Met Thr Phe Thr Ile Gly Arg Gly Asn Asp Ile Val Cys
    50                  55                  60

Ala Ala Ile Asn His Val Ala Asp Arg Leu Lys Gly Lys Lys Leu Ser
65                  70                  75                  80

Ser Leu Val Ala Asp Trp Gly Lys Thr Trp Arg Tyr Leu Val Asn Asp
                85                  90                  95

Ser Gln Leu Arg Trp Ile Gly Pro Glu Lys Gly Val Ile His Leu Ala
            100                 105                 110

Leu Gly Ala Val Val Asn Ala Val Trp Asp Leu Trp Ala Lys Thr Leu
        115                 120                 125

Asn Lys Pro Val Trp Arg Ile Val Ala Asp Met Thr Pro Glu Glu Tyr
    130                 135                 140

Val Arg Cys Ile Asp Phe Arg Tyr Ile Thr Asp Ala Ile Thr Pro Glu
145                 150                 155                 160

Glu Ala Val Ala Met Leu Arg Glu Gln Glu Ala Gly Lys Ala Lys Arg
                165                 170                 175

Ile Glu Glu Ala Leu Gln Asn Arg Ala Val Pro Ala Tyr Thr Thr Ser
            180                 185                 190

Ala Gly Trp Leu Gly Tyr Gly Glu Asp Lys Met Lys Gln Leu Leu Arg
        195                 200                 205

Glu Thr Leu Ala Ala Gly Tyr Arg His Phe Lys Val Lys Val Gly Gly
    210                 215                 220

Ser Val Glu Glu Asp Arg Arg Arg Leu Gly Ile Ala Arg Glu Ile Leu
225                 230                 235                 240

Gly Phe Asp Lys Gly Asn Val Leu Met Val Asp Ala Asn Gln Val Trp
                245                 250                 255

Ser Val Pro Glu Ala Ile Asp Tyr Met Lys Gln Leu Ser Glu Tyr Lys
            260                 265                 270

Pro Trp Phe Ile Glu Glu Pro Thr Ser Pro Asp Asp Ile Met Gly His
```

```
                275                 280                 285
Lys Ala Ile Arg Asp Ala Leu Lys Pro Tyr Gly Ile Gly Val Ala Thr
        290                 295                 300
Gly Glu Met Cys Gln Asn Arg Val Met Phe Lys Gln Leu Ile Met Thr
305                 310                 315                 320
Gly Ala Ile Asp Ile Cys Gln Ile Asp Ala Cys Arg Leu Gly Gly Val
                325                 330                 335
Asn Glu Val Leu Ala Val Leu Leu Met Ala Lys Lys Tyr Gly Val Pro
            340                 345                 350
Ile Val Pro His Ser Gly Gly Val Gly Leu Pro Glu Tyr Thr Gln His
                355                 360                 365
Leu Ser Thr Ile Asp Tyr Val Val Ser Gly Lys Leu Ser Val Leu
        370                 375                 380
Glu Phe Val Asp His Leu His Glu His Phe Leu His Pro Ser Val Ile
385                 390                 395                 400
Lys Asp Gly Tyr Tyr Gln Thr Pro Thr Glu Ala Gly Tyr Ser Val Glu
                405                 410                 415
Met Lys Pro Glu Ser Met Asp Lys Tyr Glu Tyr Pro Gly Lys Lys Gly
            420                 425                 430
Val Ser Trp Trp Thr Thr Asp Glu Ala Leu Pro Ile Leu Asn Gly Glu
        435                 440                 445
Lys Ile
    450

<210> SEQ ID NO 3
<211> LENGTH: 26
<212> TYPE: DNA
<213> ORGANISM: ARTIFICIAL SEQUENCE
<220> FEATURE:
<223> OTHER INFORMATION: PRIMER

<400> SEQUENCE: 3
ggatccacca tgtctgaagt caccat                                          26

<210> SEQ ID NO 4
<211> LENGTH: 26
<212> TYPE: DNA
<213> ORGANISM: ARTIFICIAL SEQUENCE
<220> FEATURE:
<223> OTHER INFORMATION: PRIMER

<400> SEQUENCE: 4
ggatcctcag atcttctctc cgttca                                          26

<210> SEQ ID NO 5
<211> LENGTH: 32
<212> TYPE: DNA
<213> ORGANISM: ARTIFICIAL SEQUENCE
<220> FEATURE:
<223> OTHER INFORMATION: OLIGOS

<400> SEQUENCE: 5
gagctcaagc ttccacgcag ttgctacttc ta                                   32

<210> SEQ ID NO 6
<211> LENGTH: 26
<212> TYPE: DNA
<213> ORGANISM: ARTIFICIAL SEQUENCE
<220> FEATURE:
<223> OTHER INFORMATION: OLIGOS
```

```
<400> SEQUENCE: 6
gagctctggt tatttggcag agcgac                                              26

<210> SEQ ID NO 7
<211> LENGTH: 26
<212> TYPE: DNA
<213> ORGANISM: ARTIFICIAL SEQUENCE
<220> FEATURE:
<223> OTHER INFORMATION: OLIGOS

<400> SEQUENCE: 7
actagtgggg caaagttgga catgat                                              26

<210> SEQ ID NO 8
<211> LENGTH: 32
<212> TYPE: DNA
<213> ORGANISM: ARTIFICIAL SEQUENCE
<220> FEATURE:
<223> OTHER INFORMATION: OLIGOS

<400> SEQUENCE: 8
actagtaagc ttgcaatacc tggaccaagc ta                                       32
```